United States Patent [19]
Halperin et al.

[11] Patent Number: 6,066,319
[45] Date of Patent: May 23, 2000

[54] DRUG DELIVERY USING TERMINAL COMPLEMENT COMPONENTS

[75] Inventors: Jose A. Halperin; Daniel J. Goldstein, both of Brookline; Juan A. Acosta, Boston, all of Mass.

[73] Assignee: President and Fellows of Harvard College, Cambridge, Mass.

[21] Appl. No.: 08/640,264

[22] Filed: Apr. 30, 1996

[51] Int. Cl.[7] .................................................. A61K 39/395
[52] U.S. Cl. ..................... 424/130.1; 424/184.1; 424/236.1; 514/2; 514/44; 530/387.1; 530/350; 536/22.1
[58] Field of Search ........................ 514/2, 44; 424/184.1, 424/236.1, 130.1; 530/387.1, 350; 536/22.1

[56] References Cited

U.S. PATENT DOCUMENTS

| | | | |
|---|---|---|---|
| 4,661,347 | 4/1987 | Muller-Eberhard et al. | 424/85 |
| 4,883,784 | 11/1989 | Kaneko | 514/8 |

OTHER PUBLICATIONS

Torbohm, I et al. Kidney Intl. 37: 1098–1104, 1990.
Saadi, S. et al. J. Sep. Med. 181:21–31, 1995.
John, B. et al. Immunol. 78:329–334, 1993.
Bhakdi et al., Mechanism of Complement Cytolysis and the Concept of Channel–forming proteins, *Phil. R. Soc. Lond.* B 306:311–324 (1984).
Bhakdi et al., Functions and Relevance of the Terminal Complement Sequence, *Blut* 60:309–318 (1990).
Sims, Permeability Characteristics of Complement–Damaged Membranes: . . . Proc. Natl. Acad. Sci USA 78(3):1838–1842, (1981).
Bhakdi et al., C5b–9 Assembly: Average Binding of One C9 Molecule to C5b–8 Without Poly–C9 Formation A Stable Transmembrane Pore, *J. Immunol.* 136(8):2999–3005, (1986).
Schröder et al., Pore Formation by Complement in the Outer Membrane of Gram–Negative Bacteria . . . , *J. Membrane Biol.* 118:161–170 (1990).
Bhakdi et al., Complement Lysis: Evidence for and Amphiphilic Nature of the Terminal Membrane . . . *J. Immunol.*, 121(6):2526–2532 (1978).
Bhakdi et al., Membrane Damage by Channel–Forming Proteins: Staphylococcal a–Toxin, . . . *Biochem. Soc. Symp.* 50:221–233 (1985).
Criado et al., Cytotoxic Granules from Killer Cells: Specificity of Granules . . . *J. Immunol.*, 135(6):4245–4251 (1985).
Stites et al (eds). Medical Immunol., p. 173–4, 1993.
Bloch et al, J. Immunol., 138: 842–848, 1987.
Stites et al (eds). Medical Immunol., p. 174–178, 1993.
Halperin et al., Blood 81 (1):200–205 (1993).
Li et al., J. Immunol. 152:2995–3005 (1994).
Vogel et al., Proc. Natl. Acad. Sci. USA 78 (12):7707–7711 (1981).

*Primary Examiner*—Paula K. Hutzell
*Assistant Examiner*—Minh-Tam Davis
*Attorney, Agent, or Firm*—Wolf, Greenfield & Sacks, P.C.

[57] ABSTRACT

Methods for treatment of a subject with therapeutic or diagnostic agents by delivery of the therapeutic or diagnostic agents to the subject via sublytic amounts of terminal complement membrane attack acomplex (MAC) transmembrane channels are described. Also described are methods for delivery of therapeutic or diagnostic agents to cells in vitro via sublytic amounts of MAC transmembrane channels. Pharmaceutical preparations containing MAC transmembrane channel forming agents and kits for the formation of sublytic amounts of MAC transmembrane channels also are provided.

8 Claims, No Drawings

DRUG DELIVERY USING TERMINAL COMPLEMENT COMPONENTS

BACKGROUND OF THE INVENTION

The efficient delivery of therapeutic or diagnostic agents to cells presents a vexing problem for physicians in the treatment of patients. In some cases, therapeutic or diagnostic agents are active in vitro but are not clinically effective because the therapeutic or diagnostic agents do not penetrate into cells due to physical or chemical characteristics of the therapeutic or diagnostic agents such as charge, size, or other factors. In other cases, promising therapies await the discovery of efficient delivery vehicles.

One example of the latter case is gene therapy: gene medicines for the treatment of genetic diseases are being developed at a rapid pace but the ineffectiveness of present delivery vehicles has not allowed such medicines to be applied to treatable genetic diseases. The main problems for gene therapy are the lack of appropriate systems for transferring genes to an adequate number of target cells and the difficulty of obtaining consistent expression in particular target cells which is exacerbated by the low efficiency of expression in target cells.

Current gene therapy delivery technologies rely on recombinant viral gene vectors, direct injection of plasmids into tissue, air gun delivery of DNA coated pellets or liposome mediated gene transfer. These technologies have several liabilities which result in the aforementioned inadequacies. The liabilities of the current delivery methodologies include low efficiency, risk of neoplastic transformation due to insertion in the genome of a viral vector, risk of viral vector replication, immunogenic potential of the vectors noted above, and lack of cell specificity. Other drawbacks are associated with specific viral vectors, such as the lack of insertion of retroviral vectors in nondividing cells and inflammatory reactions resulting from the use of adenoviral vectors.

Certain classes of therapeutic or diagnostic agents must be administered in doses far in excess of doses needed for efficacy on a molecular level simply due to the lack of entry of the therapeutic or diagnostic agents into cells because of physicochemical properties of the therapeutic or diagnostic agents. The high doses necessary for efficacy, however, cannot always be administered because they can result in unwanted side effects such as systemic or tissue-specific toxicities.

Administration of therapeutic or diagnostic agents with an appropriate delivery vehicle can increase the effective concentration of a therapeutic or diagnostic agent at the site where the therapeutic or diagnostic agent is needed. With more efficient delivery of a therapeutic or diagnostic agent, systemic concentrations of the agent are reduced because lesser amounts of the therapeutic or diagnostic agent can be administered while accruing the same or better therapeutic results. Methodologies applicable to increased delivery efficiency of therapeutic or diagnostic agents typically focus on attaching a targeting moiety to the therapeutic or diagnostic agent or to a carrier which is subsequently loaded with a therapeutic or diagnostic agent. These methods suffer from the drawback that each therapeutic or diagnostic agent must be either bound to a targeting moiety or loaded into a carrier, which adds extra manufacturing and regulatory costs to the therapeutic or diagnostic agent. Binding a therapeutic agent to a targeting moiety also can alter if not destroy the activity of the therapeutic agent. Moreover, delivery of a therapeutic or diagnostic agent by such prior art methods requires pharmacies to maintain stocks of therapeutic and diagnostic agents with and without one or more delivery vehicles.

Targeted delivery of therapeutic or diagnostic agents has become an important goal of practitioners of the pharmaceutical arts to limit the aforementioned side effects. For example, chemotherapeutics for the treatment of cancers typically have side effects inseparable from their mode of action, i.e. cytotoxicity to dividing cells. Strategies for increasing the efficiency of delivery to reduce toxicity to normal tissues have centered on conjugation of chemotherapeutics to monoclonal antibodies specific for cancer cells. While such methods are an improvement over other prior art methods, each new conjugate must be carefully designed and tested for specificity and activity, and approved by the U.S. Food and Drug Administration. The conjugates also suffer from vastly increased size as compared to unconjugated therapeutic or diagnostic agents, which may hinder efficient delivery of the therapeutic or diagnostic agents to cells.

There is a need, therefore, for methods to increase the efficiency of unconjugated therapeutic or diagnostic agent delivery to all tissues of the body, regardless of the size, charge, or polarity of the therapeutic or diagnostic agents. Furthermore, there is a need for delivery of therapeutic or diagnostic agents to selected tissues or cells in the body without concomitant delivery to other tissues or cell types. There is also a need for a method of delivering therapeutic or diagnostic agents more efficiently that can be used with many kinds of existing therapeutic or diagnostic agents. There is a need to provide a method of targeted delivery of therapeutic or diagnostic agents which does not require conjugation or alteration of the therapeutic or diagnostic agents which are to be delivered. It is an object of the invention to fulfill these needs.

Thus, it is a general object of the invention to provide a method for increasing the efficiency of therapeutic or diagnostic agent delivery in vivo and in vitro.

It is another general object of the invention to provide a method for selectively delivering therapeutic or diagnostic agents to specific cells without delivery of those therapeutic or diagnostic agents to other cells.

SUMMARY OF THE INVENTION

The invention involves the discovery that the terminal Membrane Attack Complex (MAC) of the complement system may be utilized, in sublytic amounts, to facilitate the delivery of therapeutic or diagnostic agents to cells in vivo and in vitro. The transmembrane channel forming properties of MAC may be utilized to nonselectively enhance cellular uptake of therapeutic or diagnostic agents. The transmembrane channel forming properties of MAC also may be utilized to selectively deliver therapeutic or diagnostic agents to specific targeted cells without concomitant delivery to non-targeted cells. Thus the invention provides methods for efficient delivery of therapeutic or diagnostic agents to any desired tissue or cell type without deleterious effects on surrounding cells as is the case with current treatments. It permits delivery of therapeutic or diagnositc agents that otherwise are not taken up by cells and it also provides enhanced uptake of therapeutic or diagnostic agents by cells that otherwise inefficiently take up such therapeutic or diagnostic agents. Safer, more effective treatments of, inter alia, pathogenic infections and neoplasms, as well as improved delivery of genetic therapies are provided by the methods of the invention.

The invention further provides isolated proteins of the complement system, such as the C5b–C6 protein complex and C3/C5 convertase as MAC transmembrane channel forming agents, in amounts sufficient for the formation of sublytic amounts of MAC transmembrane channels. The MAC transmembrane channel-forming agents may be constructed and arranged to specifically bind to defined cell types in vivo and in vitro.

According to one aspect of the invention, a method for treating a subject with a therapeutic or diagnostic agent is provided. An effective amount of a MAC transmembrane channel-forming agent is administered to a subject in need of such treatment to form sublytic amounts of MAC transmembrane channels in cells within the subject. An effective amount of the therapeutic or diagnostic agent is administered substantially simultaneously therewith. The therapeutic or diagnostic agent enters the cells through the MAC transmembrane channels. The therapeutic or diagnostic agents, when the MAC transmembrane channel-forming agent is an antibody, are non-binding to the MAC transmembrane channel forming agent. It should be recognized that the therapeutic and diagnostic agents need not be binding to the channel forming agent according to any embodiment of the invention, although such binding is not necessarily precluded according to some aspects of the invention.

In some embodiments, the MAC transmembrane channel forming agent may be constructed and arranged to selectively bind predetermined target cells within a subject to selectively deliver therapeutic or diagnostic agents to those cells. More particularly, the MAC transmembrane channel-forming agent is constructed and arranged to selectively bind to particular cells of the subject or only to cells of an infectious agent located within the subject.

In some embodiments, the MAC transmembrane channel-forming agent is an isolated C5b–C6 complement protein complex. In certain embodiments, the therapeutic or diagnostic agent is a therapeutic agent selected from the group consisting of polypeptides, oligonucleotides, toxins and antibiotics, antivirals, antiparasitics, antifungals and anticancer agents. In one particular embodiment, the therapeutic agent is a therapeutic oligonucleotide.

The invention in another aspect involves a method for the delivery of a therapeutic or diagnostic agent to a cell in vitro. The cell is contacted in vitro with an effective amount of a MAC transmembrane channel-forming agent to form a sublytic amount of MAC transmembrane channels in the cell, and, substantially simultaneously therewith, contacted with an effective amount of the therapeutic or diagnostic agent. The therapeutic or diagnostic agent enters the cells through the MAC transmembrane channels and, when the MAC transmembrane channel-forming agent is an antibody, is non-binding with respect to the MAC transmembrane channel-forming agent. As with in vivo applications, the therapeutic and diagnostic agents may not be binding to the channel forming agent according to any in vitro embodiment of the invention, although such binding is not necessarily precluded according to some aspects of the invention.

In preferred in vitro embodiments, the MAC transmembrane channel-forming agent is an isolated C5b–C6 complement protein complex. Preferably the cell also is contacted with an isolated C7 complement protein and with isolated C8 and C9 complement proteins.

In another embodiment, the MAC transmembrane channel-forming agent is an isolated C3/C5 convertase. Preferably the C3/C5 convertase is constructed and arranged to selectively bind to target cells. In yet another embodiment, the MAC transmembrane channel-forming agent is a plurality of an antibody coupled to a crosslinkable agent. After the antibody has bound to the target cells, crosslinking agents are added to the environment of the cells to crosslink the crosslinkable agent and initiate the formation of the MAC transmembrane channel.

In another aspect, the invention furnishes pharmaceutical preparations. The pharmaceutical preparation includes an effective but sublytic amount of isolated C5b–C6 complement protein complex and a pharmaceutically acceptable carrier.

According to another aspect of the invention, kits for forming MAC transmembrane channels in a cell are provided. Preferably, the kit includes a first container containing isolated C5b–C6, a second container containing isolated C7 complement protein, a third container containing isolated C8 complement protein and a fourth container containing isolated C9 complement protein, along with instructions for forming MAC transmembrane channels in the cell. In another embodiment, the first container contains isolated C5 complement protein, and a fifth container containing isolated C6 complement protein, a sixth container containing cobra venom factor, a seventh container containing factor B and an eighth container containing factor D are provided along with instructions for preparing C5b–C6 protein complex.

DETAILED DESCRIPTION OF THE INVENTION

The membrane attack complex (MAC) is a heteropolymeric complex of terminal complement proteins C5b, C6, C7, C8 and C9 which assembles in a lipid bilayer, such as a cell membrane, to allow the passage of molecules through the bilayer. Upon insertion into a membrane, the MAC components form a transmembrane channel in the form of a hollow cylinder having hydrophilic protein domains disposed on the interior of the channel and hydrophobic protein domains disposed on the exterior of the channel. The effective internal radius of the MAC transmembrane channel is about 5–10 nm, sufficient to allow the passage of many polypeptide growth factors and cytokines, such as platelet derived growth factor (PDGF), beta-fibroblast growth factor (bFGF) and gamma interferon (IFNγ). (It is more than large enough to permit passage of typical small drug molecules.) The MAC transmembrane channel is transient in nature, having a half-life of about 3 minutes; the channel is eliminated by endocytosis, membrane shedding or spontaneous closure of the channel. If enough channels have been formed, the cell is disabled by the influx of molecules through the channel, typically followed by lysis.

The invention concerns the discovery that MAC transmembrane channels may be used, in sublytic amounts, to increase the delivery of therapeutic or diagnostic agents. The formation of MAC transmembrane channels in cells is initiated by administration of an effective amount of a MAC transmembrane channel forming agent. An "effective amount" of a MAC transmembrane channel forming agent is an amount which effects a desired phenomenon or event without causing excessive, undesired or unrelated events or phenomena to occur. An effective amount of a MAC transmembrane channel forming agent is an amount sufficient to cause formation of a MAC transmembrane channel in a lipid bilayer membrane in the presence of terminal complement proteins. An effective amount of a MAC transmembrane channel forming agent, however, is less than an amount which disables and/or causes lysis of a cell (hereinafter a sublytic amount of MAC transmembrane channel forming agent). As will be described in the examples below, an effective amount of a MAC transmembrane channel forming agent causes an increase in the cell's uptake of compounds without associated cell lysis.

An effective amount of a therapeutic or diagnostic agent is administered substantially simultaneously to a cell with the MAC transmembrane channel forming agent. In this context, an effective amount of a therapeutic or diagnostic agent is an amount which causes a desired effect on the cell to which it is administered. The desired effect may be cytotoxicity, alteration of cell phenotype, visualization of the cell, and many other effects. Substantially simultaneously means close enough in time such that the therapeutic or diagnostic agent is present when the transmembrane agents are present.

The MAC transmembrane channel formation requires C5b protein which may be formed from the cleavage of C5 to C5a and C5b by C3/C5 convertase or another convertase enzyme such as cobra venom factor. Of course, C5b protein may be prepared by recombinant methodologies as are well known to one of ordinary skill in the art. C5b, however, is relatively unstable. C5b protein binds C6 protein to form a relatively stable C5b–C6 protein complex. This complex is the essential and first component for forming the MAC transmembrane channel. C7, C8 and one or more C9 protein molecules associate with the C5b–C6 complex to form the membrane-inserted protein complex conventionally known as MAC (Roitt, *Essential Immunology*, 7th Edition, Blackwell Scientific Publications, Oxford). The C5b–C6 complex binds to C7 protein as the first step in MAC transmembrane channel formation. Binding of C5b–C6 and C7 causes expression of a hydrophobic domain which allows insertion into lipid bilayers. The order of administration of C5b-6 and C7 is not important, but the isolated C5b-6 and isolated C7 should not be mixed prior to administration (and preferably are not administered simultaneously) due to the transient expression of the aforementioned hydrophobic domain. C8 and C9 proteins are administered after the formation of the C5b–C6–C7 protein complex, or may be administered with C7 after administration of C5b–C6. For administration in vivo to a subject, the source of C7, C8, or C9 protein may be isolated proteins or, if desired, the endogenous C7, C8 or C9 proteins of the subject. For contacting cells in vitro, the C7, C8 or C9 proteins may be supplied by serum or as isolated proteins. C8 and C9 proteins may be mixed prior to administration, and a C8–C9 mixture optionally may contain therapeutic or diagnostic agents to be delivered through the MAC transmembrane channel.

The invention thus involves initiating the formation of MAC transmembrane channels, in sublytic amounts, to provide access by therapeutic and diagnostic agents into cells via these channels. An agent which initiates the formation of a MAC transmembrane channel is a "MAC transmembrane channel forming agent" as used herein. As noted above, C3/C5 convertase is a MAC transmembrane channel forming agent because it causes the formation of C5b which associates with C6 to form the essential C5b–C6 protein complex. The use of C3/C5 convertase for mobilization of host cytotoxic mechanisms against specific cellular targets has been described previously in U.S. Pat. No. 4,661,347. In that patent, C3/C5 convertase was targeted to specific cells in a host, by conjugation to a molecule having binding affinity to a surface structure of a target cell, to kill the cells by inducing the formation of lytic amounts of MAC transmembrane channels. The use of another convertase enzyme, cobra venom factor, for the purpose of lysing cells was also disclosed in that patent.

Other proteins which have non-constitutive C3/C5 convertase activity may also serve as MAC transmembrane channel forming agents for in vivo uses. (Constitutive C3/C5 convertase activity, however, is not consistent with the formation of a sublytic amount of MAC transmembrane channels in vivo. For example, natural cobra venom factor (CVF) is not a useful MAC transmembrane channel forming agent in vivo, although it may be useful in vitro for the formation of a MAC transmembrane channel forming agent such as C5b–C6 complex, because it is not regulated or metabolized in vivo. As a constitutive and non-regulatable C3/C5 convertase it would convert all C5 present in the body to C5a and C5b and would form lytic amounts of transmembrane channels. Thus, CVF in its natural form, that is, having unregulated activity, is not useful in vivo as a MAC transmembrane channel forming agent, although a modified CVF which can be regulated to be non-constitutive could be useful as a MAC transmembrane channel forming agent in vivo.)

Another MAC transmembrane channel forming agent is isolated C5b–C6 protein complex. When added alone to cells in vivo or together with C7–C9 in vitro (as described in greater detail above), C5b–C6 protein complex also initiates the formation of a MAC transmembrane channel in cells. Still another MAC transmembrane channel forming agent is perforin, a molecule closely related to C9 (90% homology) which by itself forms pores in membranes. Other MAC transmembrane channel forming agents include antibodies which can be crosslinked at the extracellular surface of a cell membrane, and microbial polysaccharides targeted to the extracellular surface of the cell membrane as described herein with C3/C5 convertase targeting. Such MAC transmembrane forming agents serve as a nucleation site for the formation of the C5b–C6 complex and the assembly of a complete MAC transmembrane channel.

To initiate MAC transmembrane channel formation by antibodies, antibodies once bound to a cell must associate in groups. Monoclonal antibodies are particularly weak initiators of MAC transmembrane channel formation in this regard. Therefore, MAC transmembrane channel formation by the use of antibodies as MAC transmembrane channel forming agents may be effected by coupling the antibodies to a crosslinkable agent. The crosslinkable agent can cause the association of the antibodies, particularly monoclonal antibodies, at the surface of the cell. A "crosslinkable agent", as used herein, is an agent which may be crosslinked upon the addition of an appropriate crosslinking agent. Preferably, the crosslinking agent and the crosslinkable agent form a specific binding pair such that the crosslinkable agent is not crosslinked except in the presence of the specific crosslinking agent. Examples of crosslinkable agent-crosslinking agent binding pairs are biotin-avidin, biotin-streptavidin, biotin-NeutrAvidin (Pierce, Rockford, Ill.), nucleic acids of defined sequence and nucleic acid binding proteins which bind to the defined sequence (e.g., transcription factors), association domains of proteins (e.g., leucine zippers), and epitope-paratope pairs. Other pairs of crosslinkable agents and crosslinking agents will be known to one of ordinary skill in the art. The suitability of any crosslinkable agent crosslinking agent pair as an enhancer of antibody aggregation for initiating MAC transmembrane channel formation can be tested by one of ordinary skill in the art with no more than routine experimentation.

To enhance MAC transmembrane channel formation by an antibody MAC transmembrane channel forming agent as described above, a crosslinking agent which is effective in crosslinking the crosslinkable agent may be added to the environment of the cell. By "added to environment of the cell", it is meant that the cells to which the antibody is bound should be exposed to the crosslinking agent. The crosslinking agent may be added generally, e.g. systemically, so that it contacts the environment of all cells. Because only antibodies linked to a crosslinkable agent will be crosslinked, MAC transmembrane channels will be formed only in those cells to which antibodies coupled to a crosslinkable agent are bound. If desired administration of the crosslinking agent may be localized.

Antibodies useful as MAC transmembrane channel-forming agents may be polyclonal or monoclonal, and as described above, may be fragments of antibodies as long as the antibody induces MAC transmembrane channel formation. Antibodies useful in the manufacture of MAC transmembrane channel forming agents may be isolated according to methods known to one of ordinary skill in the art. For example, monoclonal antibodies may be prepared according to standard methods first developed by Kohler and Milstein (see, e.g. *Antibodies*, Harlow and Lane, Eds.). Human antibodies may be produced and isolated according to the methods disclosed in PCT International Patent Application WO 94/06448.

Formation of MAC transmembrane channels according to the invention requires a supply of terminal complement proteins described previously in addition to a MAC transmembrane channel forming agent. Administration of a MAC transmembrane channel forming agent alone is sufficient to form MAC transmembrane channels in vivo, as the subject's endogenous complement proteins provide the components required for formation of the channel. Of course, if the endogenous complement proteins are inadequate in amount or function, then exogenous complement proteins may be administered. Exogenous complement proteins may be recombinant, isolated from a natural source, or present in, and administered as, serum. When forming MAC transmembrane channels in vitro, some or all of the complement proteins which form the MAC transmembrane channel must be added. If formation of a MAC transmembrane channel in vitro is initiated by the C5b–C6 protein complex as a MAC transmembrane channel forming agent, then complement proteins C7, C8 and C9 must be added. If one uses a MAC transmembrane channel forming agent which forms the C5b-6 complex in vitro, then C5, C6, C7, C8 and C9 complement proteins must be supplied. As noted above, the proteins may be supplied by serum or may be supplied as isolated proteins prepared by methods standard in the art.

In preferred embodiments, the MAC transmembrane channel forming agent is constructed and arranged to selectively bind to a specific cell type or types. The moiety which confers selective binding is known in the art as a targeting agent. The targeting agent binds covalently or noncovalently to a cell surface molecule which is characteristic of the targeted cell. When administering the MAC transmembrane channel forming agent to a subject in vivo, for example, formation of MAC transmembrane channels for delivery of a therapeutic or diagnostic agent may be restricted to only those cell types desired, by linkage of the MAC transmembrane channel forming agent to a targeting agent. Targeted cell types may be part of normal tissue of the host, may be diseased host tissue, or may be present in the host as part of an infection. For example, an oligonucleotide useful in gene therapy may be delivered via selective transmembrane channel formation only in certain desired cell types, e.g. progenitor cells for tissues affected by the gene defect. As another example, antibiotic therapeutic agents may be delivered via selective transmembrane channel formation only in pathogenic bacteria without delivery to host cell or to normal intestinal bacteria.

Delivery of therapeutic or diagnostic agents to cells in vitro is similar to the method described above for in vivo delivery of therapeutic or diagnostic agents. As used herein, "in vitro" includes application of the invention to cells in culture (e.g. in cell culture dishes, flasks, bottles or fermenters) as well as application of the invention to cells ex vivo wherein the cells treated according to the invention are taken from within the subject but treated apart from the subject. In certain ex vivo embodiments of the invention, the cells are taken from within the subject, treated according to the invention and returned to the subject without any additional culture steps. In other ex vivo embodiments, the cells from within the subject may be cultured or treated apart from the subject prior to treatment according to the invention.

All cells in an in vitro culture system may be contacted with a sublytic amount of a MAC transmembrane channel forming agent. Alternatively, one or more types of cells in a mixed cell culture may be targeted for formation of MAC transmembrane channels. For example, bacterial contamination of a culture may be reduced or eliminated by selective formation of MAC transmembrane channels in the bacterial cells and the addition of antibacterial therapeutic compounds. Thus, contaminating cells may be destroyed with minimal damage to other cells in the culture.

Targeting of MAC transmembrane channel forming agents by the aforementioned targeting agents may increase the specificity and selectivity of formation of MAC transmembrane channels. Targeting of the MAC transmembrane channel forming agent thus permits increased selectivity and specificity in the delivery of therapeutic or diagnostic agents to cells. The skilled artisan thus may choose the cells to which the therapeutic or diagnostic agents are preferentially delivered, and the therapeutic or diagnostic agent may be delivered via MAC transmembrane channels preferentially to those cells and not to other cells. The choice of the targeting agent determines the scope of the selectivity and specificity of therapeutic or diagnostic agent delivery, i.e. whether one, two or more cell types are subject to MAC transmembrane channel formation and delivery of therapeutic or diagnostic agents.

The target of the MAC transmembrane channel forming agent can be any kind of cell or particle that has a lipid bilayer membrane, including mammalian cells, bacterial cells, parasitic cells, fungal cells and viruses. MAC transmembrane channels can also be formed according to the methods of the invention in liposomes or other lipid bilayer structures.

Targeting agents useful in the invention include, but are not limited to, antibodies to cell surface proteins, ligands to cell surface proteins, lectins and the like (see, e.g., U.S. Pat. Nos. 4,661,347; 4,671,958; and 5,334,761). For targeting purposes when using antibodies, any fragment which confers specific binding to a MAC transmembrane channel forming agent is useful in the invention, including whole monoclonal and polyclonal antibodies, as well as effective fragments thereof such as Fab, F(ab)$'_2$, Fv and other epitope binding fragments thereof. Single chain antibodies, humanized antibodies, bifunctional antibodies, chimeric antibodies and other such entities also may be used according to the invention. Likewise synthetic peptides with binding specificity are useful according to the invention. Cloned receptors that recognize cell surface molecules also may be used. Likewise, ligands of cell surface molecules are useful for targeting MAC transmembrane channel forming agent.

Ligands include growth factors and cytokines like IL-1 to IL-12, TGF-α, tumor necrosis factor, epidermal growth factor, platelet derived growth factor, transferrin and transcobalamin. Targeting moieties also include those molecules on the surface of mammalian cells that are recognized by pathogens. Conversely, surface molecules of pathogens that interact with mammalian cell surface proteins, such as gp120 of HIV, may be employed as targeting moieties. Other similar targeting moieties will be apparent to one of ordinary skill the art.

In other embodiments, the targeting moiety may be more than a single molecule, and, in particular, may be an encapsulating particle that has the ability to target the delivery of the contents of the particle to a desired location and, simultaneously, encapsulate the MAC transmembrane channel forming agent for delivery to the target. Such "particles" include viruses, bacteria, liposomes, red blood cell ghosts and the like. Methods for the encapsulation of compounds in such particles are well known in the art. For example, a virus particle may be formed around any MAC transmembrane channel forming agent chosen by incubation of the nucleic acid with sufficient viral coat proteins. Similarly, liposomes spontaneously form around the constituents of the solution with which the precursor lipids are combined.

For certain embodiments of the invention as described above, the MAC transmembrane channel forming agent is "linked to" a targeting moiety. Such "linkage" is useful for binding one or more targeting agents to one or more MAC transmembrane channel forming agents for the selective targeting of the MAC transmembrane channel forming agent to a particular cell or other lipid bilayer enclosed particle. As used herein, "linked" or "linkage" means two entities are bound to one another by any physicochemical means. It is important that the linkage be of such a nature that it does not impair substantially the effectiveness of the MAC transmembrane channel forming agent or the binding specificity of the targeting molecule. Keeping these parameters in mind, any linkage known to those of ordinary skill in the art may be employed, whether covalent or noncovalent.

Linkage according to the invention need not be direct linkage. A MAC transmembrane channel forming agent and a discrete targeting moiety may be provided with functionalized groups to facilitate their linkage and/or linker groups may be interposed between the MAC transmembrane channel forming agent and the targeting moeity to facilitate their linkage. In addition, the MAC transmembrane channel forming agent and the targeting moiety may be synthesized in a single process, whereby the MAC transmembrane channel forming agent and the targeting moiety could be regarded as one and the same entity. For example, a targeting molecule specific for an extracellular receptor could be synthesized together with the MAC transmembrane channel forming agent e.g., as a single fusion polypeptide prepared according to standard methods in the art.

Linkage may also be conferred by a specific molecule that provides a covalent or noncovalent bond between a MAC transmembrane channel forming agent and a targeting moiety. Specific examples of covalent bonds include those wherein bifunctional crosslinker molecules are used. The crosslinker molecules may be homobifunctional or heterobifunctional, depending upon the nature of the molecules to be linked. Homobifunctional crosslinkers have two identical reactive groups. Heterobifunctional crosslinkers have two different reactive groups that allow for sequential conjugation reaction. Various types of commercially available crosslinkers are reactive with one or more of the following groups; primary amines, secondary amines, sulfhydryls, carboxyls, carbonyls and carbohydrates. Examples of amine-specific crosslinkers are bis(sulfosuccinimidyl) suberate, bis[2-(succinimidooxycarbonyloxy)ethyl]sulfone, disuccinimidyl suberate, disuccinimidyl tartarate, dimethyl adipimate·2 HCl, dimethyl pimelimidate·2 HCl, dimethyl suberimidate·2 HCl, and ethylene glycolbis-[succinimidyl-[succinate]]. Crosslinkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido) butyl]-3'-[2'-pyridyldithio]propionamide. Crosslinkers preferentially reactive with carbohydrates include azidobenzoyl hydrazide. Crosslinkers preferentially reactive with carboxyl groups include 4-[p-azidosalicylamido]butylamine. Heterobifunctional crosslinkers that react with amines and sulfhydryls include N-succinimidyl-3-[2-pyridyldithio] propionate, succinimidyl[4-iodoacetyl]aminobenzoate, succinimidyl 4-[N-maleimidomethyl] cyclohexane-1-carboxylate, m-maleimidobenzoyl-N-hydroxysuccinimide ester, sulfosuccinimidyl 6-[3-[2-pyridyldithio] propionamido]hexanoate, and sulfosuccinimidyl 4-[N-maleimidomethyl] cyclohexane-1-carboxylate. Heterobifunctional crosslinkers that react with carboxyl and amine groups include 1-ethyl 3-[3-dimethylaminopropyl]-carbodiimide hydrochloride. Heterobifinctional crosslinkers that react with carbohydrates and sulfhydryls include 4-[N-maleimidomethyl]-cyclohexanel-carboxylhydrazide·HCl, 4-(4-N-maleimidophenyl)-butyric acid hydrazide·HCl, and 3-[2-pyridyldithio]propionyl hydrazide. The crosslinkers may also be nonselective. Examples of nonselective crosslinkers are bis-[β-(4-azidosalicylamido)ethyl]disulfide and glutaraldehyde.

Noncovalent linkage may also be used to join the MAC transmembrane channel forming agent and the targeting moiety. Noncovalent linkage may be accomplished by direct or indirect means including hydrophobic interactions, ionic interactions of positively and negatively charged molecules, and other affinity interactions. One of ordinary skill in the art may easily determine which noncovalent linkages are useful for linking a particular MAC transmembrane channel forming agent and targeting moeity for targeting the MAC transmembrane channel forming agent to a particular cell.

Molecules comprising MAC transmembrane channels or MAC transmembrane channel forming agents may be variants of the polypeptides specifically disclosed herein. A "variant" of a polypeptide includes a molecule substantially similar in structure to the polypeptide, or to a fragment thereof. Variants of polypeptides include those examples with conservative amino acid substitutions, small insertions or deletions, or additions to the amino or carboxyl termini of the polypeptide. Thus, substitutions of structurally similar amino acids in proteins, such as leucine for isoleucine, or insertions, deletions, and terminal additions which do not destroy the functional utility of the protein are contemplated. The production of such variants is well known in the art and, therefore, such variants are intended to fall within the scope of the invention.

The therapeutic or diagnostic agents administered according to the methods of the invention are non-binding to the MAC transmembrane channel forming agent when the MAC transmembrane channel forming agent is an antibody. By "non-binding" it is meant that the therapeutic or diagnostic agent is not bound, complexed or linked in any way to the MAC transmembrane channel forming agent when administered to a subject or cell, i.e., the therapeutic or diagnostic agent is administered as a separate molecule distinct from the MAC transmembrane channel forming agent. The therapeutic or diagnostic agent can be non-binding to the MAC transmembrane channel forming agent irrespective of whether the MAC transmembrane channel forming agent is an antibody.

In certain embodiments, the MAC transmembrane channel forming agent is isolated C5b–C6 complement protein complex or isolated C3/C5 convertase. In some embodiments, isolated terminal complement proteins also are added or administered. Isolated terminal complement proteins thus may be supplied in kits to form MAC transmembrane channels in a cell. As used herein, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other complement proteins.

The methods of the invention disclosed herein increase the efficiency of delivery of therapeutic or diagnostic agents to cells, particularly to cells which take up such therapeutic or diagnostic agents inefficiently. For example, application of the methods of the invention enables the safe use of therapeutic compounds which at high doses have associated toxicity because increased efficiency of uptake in cells having MAC transmembrane channels permits lower doses of such therapeutic compounds to be administered to a subject.

The invention provides improved methods for treating a subject with therapeutic or diagnostic agents and for delivering therapeutic or diagnostic agents to a cell. The agents to be delivered or administered may be any therapeutic or diagnostic agents which pass through the MAC transmembrane channels. The properties of the molecule or molecules comprising the therapeutic or diagnostic agents is of no importance so long as the molecule can pass through the MAC transmembrane channels. Thus, therapeutic or diagnostic agents deliverable by the methods of the invention may be charged or uncharged, polar or nonpolar, globular or rod-like, natural or non-natural, and the like. In preferred embodiments, the therapeutic or diagnostic agents are selected from the group consisting of polypeptides, oligonucleotides, toxins, antibiotics, antivirals and antiparasitics.

Polypeptides useful as therapeutic or diagnostic agents may be of any sequence and size which will pass through the MAC transmembrane channels formed by the methods disclosed herein. The polypeptides may be isolated natural or non-natural proteins or peptides. In the context of polypeptides used herein, non-natural is intended to encompass polypeptides which have one or more: synthetic linkages between amino acids (i.e. non-peptide bonds), non-natural amino acids including D-amino acids, branched amino acid linkages, and non-amino acid components.

The methods disclosed herein are particularly suited to delivery of polypeptides of therapeutic benefit, such as hormones including calcitonin, growth hormone, thyrotropic hormone, corticotropin, chorionic gonadotropin, somatostatin, glucagon and insulin, immunosuppressants including cyclosporin, antineoplastic drugs including dactinomycin and luteinizing hormone releasing factor, and cytokines including interleukins, interferons, GM-CSF, CSF, erythropoietin, TGF-$\alpha$, TGF-$\beta$, TNF and the like.

Oligonucleotides also are useful in the invention as therapeutic or diagnostic agents. Oligonucleotides in this context may be antisense oligonucleotides or sense oligonucleotides, e.g. oligonucleotides which encode polypeptides. Oligonucleotides, as used herein, also encompass nucleic acid sequences operably joined to regulatory sequences, e.g. nucleic acids conventionally known as vectors. Oligonucleotides may be "natural" or "modified" with regard to subunits or bonds between subunits. In preferred embodiments, the oligonucleotide is a therapeutic oligonucleotide.

A therapeutic oligonucleotide is one which provides to the subject a therapeutic benefit. A therapeutic benefit may be an alteration of cell proliferation, a change of expression of a single or multiple genes or proteins, a cytotoxic effect against a pathogen, inhibition of viral replication, replacement of a defective gene and the like. Therapeutic oligonucleotides may be administered in the form of an oligonucleotide operably joined to regulatory sequences, disposed in a vector for replication or regulated expression, or in separate nonoperable pieces that can join in the cell to yield an operable expression system as disclosed in PCT International Patent Application WO 93/23553. Therapeutic oligonucleotides may be linked to other oligonucleotides, either therapeutic or nontherapeutic by methods which are standard in the art, as will be described below. Therapeutic oligonucleotides may also be linked to a non-oligonucleotide therapeutic or diagnostic agent which can provide additional therapeutic benefit to the subject or cell. One example of a therapeutic oligonucleotide is an antisense oligonucleotide.

An antisense oligonucleotide is constructed and arranged so as to interfere with transcription or translation of a desired target oligonucleotide upon hybridization with the target. Those skilled in the art will recognize that the exact length of the antisense oligonucleotide and its degree of complementarity will depend upon the specific target selected, including the sequence of the target and the particular bases which comprise that sequence. It is preferred that the antisense oligonucleotide be selected so as to hybridize selectively with the target under physiological conditions, i.e., to hybridize substantially more with the target sequence than with any other sequence in the target cell under physiological conditions.

In one set of embodiments, oligonucleotides useful in the methods of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer.

In other embodiments, however, the oligonucleotides also may include "modified" oligonucleotides. That is, the oligonucleotides may be modified in a number of ways which do not prevent them from e.g., hybridizing to their target, or being translated or transcribed, but which enhance their stability or targeting or which otherwise enhance their therapeutic effectiveness. The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptide linkages.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding osteoclast transporter proteins, together with pharmaceutically acceptable carriers.

Another example of a therapeutic oligonucleotide is one which includes regulatory sequences operably linked to coding sequences. As used herein, a coding sequence and regulatory sequences are said to be operably joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences, as desired.

As used herein, a vector may be any of a number of nucleic acids into which a desired oligonucleotide may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired oligonucleotide may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired oligonucleotide may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

Ribozymes also may be efficiently delivered by use of the methods disclosed herein. Ribozymes are enzymatic oligonucleotides which cleave other oligonucleotides, particularly messenger RNA molecules. For example, ribozymes are described in U.S. Pat. No. 4,987,071 (Cech). Ribozymes may be composed of natural subunits with naturally occurring bonds between the subunits, or may have non-naturally occurring subunits and bonds, or a mixture of natural and non-natural subunits and bonds therebetween according to the needs of the skilled artisan. The specificity of the ribozyme may also be selected according to the needs of the investigator.

The present invention can be utilized for the efficient delivery of toxins. The toxins will enter a cell via a MAC transmembrane channel formed according to the invention. Toxins may be administered with or without coupling to hydrophilic carrier molecules such as dextran. Toxins can be proteins such as, for example, pokeweed anti-viral protein, cholera toxin, pertussis toxin, ricin, gelonin, abrin, diphtheria exotoxin, or Pseudomonas exotoxin. Toxin moieties can also be high energy-emitting radionuclides such as cobalt-60.

Antibiotics may also be delivered with greater efficiency, specificity and selectivity according to the methods described herein. Antibiotic therapeutics useful in the invention include, but are not limited to, anti-bacterial therapeutics, anti-viral therapeutics, anti-parasitic therapeutics, anti-fungal therapeutics, anti-malarial therapeutics and amebicide therapeutics.

Anti-bacterial therapeutics are well known and include: penicillins, ampicillin, amoxicillin, cyclacillin, epicillin, methicillin, nafcillin, oxacillin, cloxacillin, dicloxacillin, flucloxacillin, carbenicillin, cephalexin, cepharadine, cefadoxil, cefaclor, cefoxitin, cefotaxime, ceftizoxime, cefinenoxine, ceftriaxone, moxalactam, imipenem, clavulanate, timentin, sulbactam, erythromycin, neomycin, gentamycin, streptomycin, metronidazole, chloramphenicol, clindamycin, lincomycin, quinolones, rifampin, sulfonamides, bacitracin, polymyxin B, vancomycin, doxycycline, methacycline, minocycline, tetracycline, amphotericin B, cycloserine, ciprofloxacin, norfloxacin, isoniazid, ethambutol, and nalidixic acid.

Anti-viral therapeutics are well known and include: acyclovir, idoxuridine, ribavirin, trifluridine, vidirabine, dideoxucytidine, dideoxyinosine, zidovudine and gancyclovir.

Anti-parasitic therapeutics (parasiticides) are well known and include: bithionol, diethylcarbamazine citrate, mebendazole, metrifonate, niclosamine, niridazole, oxamniquine, piperazine citrate, praziquantel, pyrantel pamoate and thiabendazole.

Anti-fimgal therapeutics are well known and include: amphotericin B, clotrimazole, econazole nitrate, flucytosine, griseofulvin, ketoconazole and miconazole.

Anti-malarial therapeutics are well known and include: chloroquine HCl, primaquine phosphate, pyrimethamine, quinine sulfate and quinacrine HCl.

Amebicide therapeutics are well known and include: dehydroemetine dihydrochloride, iodoquinol and paromomycin sulfate.

Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-$\alpha$, lomustine, mercaptopurine, methotrexate, mitotane, procarbazine HCl, thioguanine, vinblastine sulfate and vincristine sulfate.

Antimicrobial agents can be nucleic acids that effect a reduction or an increase of synthesis of specific gene products. For example, an antimicrobial agent may be a plasmid which directs the synthesis of a protein which is toxic to bacterial cells. Such a toxin preferably will not affect the host infected with the bacterial cells targeted by the toxin. As another example, antimicrobials may be antisense oligonucleotides or catalytic nucleic acids, including ribozymes. An effective quantity of such nucleic acid antimicrobial compounds may be sufficient to reduce expression of gene products critical to the growth or survival of bacterial cells, such as components of the cell wall, cell membrane, nutrient transport or synthesis systems, protein synthesis apparatus, nucleic acid synthesis apparatus, and the like.

Other compounds deliverable by the composition of the invention may be effective as antimicrobial agents by potentiating the effects of antibiotics standard in the medical arts. Such potentiating compounds may be effective as antimicrobial agents when delivered alone. Examples of potentiating agents include inducers of receptors for antibiotics, agents which increase transport of antibiotics into bacterial cells or decrease transport of antibiotics out of bacterial cells, inhibitors of bacterial enzymes which metabolize antibiotics, and the like.

As noted above, efficient administration of a variety of therapeutic and diagnostic agents is made possible by the methods of the invention. It is contemplated that therapeutic modalities for treatment of diseases of many different etiologies will be improved by the use of these methods. Such diseases include organ and cell specific inborn errors of metabolism, acquired deficiencies of specific hormones e.g. anemias requireing continuous production of erythropoietin, vascular thrombotic diseases, acquired immune deficiency syndrome and non-neoplastic pathological conditions associated with abnormal apoptosis such as preneoplastic lymphoproliferative or erythroproliferative syndromes. Improved treatments of cancer are also contemplated, including treatment of the primary tumor by control of tumoral cell proliferation, angiogenesis, metastatic growth, or apoptosis, and treatment of the development of macrometastasis after removal of the primary tumor. Treatment of non-neoplastic pathological conditions associated with cell proliferation may also be performed in accordance with the invention, including conditions such as atherosclerosis, arteriosclerosis, hemangiomas, vascular dysplasias, restenosis, diabetes mellitus, organ transplants and autoimmune diseases such as rheumatoid arthritis, systemic lupus erythematosus and autoimmune vasculitis.

Examples of important pathogens to which therapeutic agents may be specifically delivered include *Vibrio cholerae*, enterotoxigenic *Escherichia coli*, rotavirus, *Clostridium difficile*, Shigella species, *Salmonella typhi*, parainfluenza virus, influenza virus, *Streptococcus pneumoniae*, *Borella burgdorferi*, HIV, *Streptococcus mutans*, *Plasmodiumfalciparum*, *Staphylococcus aureus*, rabies virus and Epstein-Barr virus. Other pathogens, as noted below, can be the recipients of sublytic amounts of MAC transmembrane channel forming agents accoding to the methods of the invention.

Viruses in general include but are not limited to those in the following families: picomaviridae; caliciviridae; togaviridae; flaviviridae; coronaviridae; rhabdoviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae; and poxyviridae.

Bacteria in general include but are not limited to: *P. aeruginosa*; *E. coli*; Klebsiella sp.; Serratia sp.; Pseudomonas sp.; *P. cepacia*; Acinetobacter sp.; *S. epidermis*; *E. faecalis*; *S. pneumoniae*; *S. aureus*; Haemophilus sp.; Neisseria sp.; *N. meningitidis*; Bacteroides sp.; Citrobacter sp.; Branhamella sp.; Salmonella sp.; Shigella sp.; *S. pyogenes*; Proteus sp.; Clostridium sp.; Erysipelothrix sp.; Lesteria sp.; *Pasteurella multocida*; Streptobacillus sp.; Spirillum sp.; Fusospirocheta sp.; *Treponema pallidum*; Borrelia sp.; Actinomycetes; Mycoplasma sp.; Chlamydia sp.; Rickettsia sp.; Spirochaeta; Legionella sp.; Mycobacteria sp.; Ureaplasma sp.; Streptomyces sp.; Trichomoras sp.; and *P. mirabilis*.

Parasites include but are not limited to: Plasmodiumfalciparum, *P. vivax*, *P. ovale*, *P. malaria*; *Toxoplasma gondii*; *Leishmania mexicana*, *L. tropica*, *L. major*, *L. aethiopica*, *L. donovani*; *Trypanosoma cruzi*, *T brucei*; *Schistosoma mansoni*, *S. haematobium*, *S. japonium*; *Trichinella spiralis*; *Wuchereria bancrofti*; *Brugia malayi*; *Entamoeba histolytica*; *Enterobius vermiculoarus*; *Taenia solium*, *T saginata*; *Trichomonas vaginatis*, *T hominis*, *T. tenax*; *Giardia lamblia*; *Cryptosporidium parvum*; *Pneumocytis carinii*; *Babesia bovis*, *B. divergens*, *B. microti*; *Isospora belli*, *I. hominis*; *Dientamoebafragilis*; *Onchocerca volvulus*; *Ascaris lumbricoides*; *Necator americanis*; *Ancylostoma duodenale*; *Strongyloides stercoralis*; *Capillaria philippinensis*; *Angiostrongylus cantonensis*; *Hymenolepis nana*; *Diphyllobothrium latum*; *Echinococcus granulosus*, *E. multilocularis*; *Paragonimus westermani*, *P. caliensis*; *Chlonorchis sinensis*; *Opisthorchisfelineus*, *O. viverrini*; *Fasciola hepatica*; *Sarcoptes scabiei*; *Pediculus humanus*; *Phthirius pubis*; and *Dermatobia hominis*.

Fungi in general include but are not limited to: *Cryptococcus neoformans*; *Blastomyces dermatitidis*; *Ajellomyces dermatitidis*; *Histoplasma capsulatum*; *Coccidioides immitis*; Candida species, including *C. albicans*, *C. tropicalis*, *C.*

*parapsilosis, C. guilliermondii* and *C. krusei*; Aspergillus species, including *A. fumigatus, A. flavus* and *A. niger*; Rhizopus species; Rhizomucor species; Cunninghammella species; Apophysomyces species, including *A. saksenaea, A. mucor* and *A. absidia; Sporothrix schenckii; Paracoccidioides brasiliensis; Pseudallescheria boydii; Torulopsis glabrata*; and Dermatophytes species.

Diagnostic agents are also administrable to cells within a subject by the methods of the invention. As with therapeutic agents, the administration of diagnostic agents to cells via MAC transmembrane channels enables the use of lesser amounts of diagnostic agents for equivalent diagnostic efficacy, thus reducing associated side effects and complications resulting from the diagnostic agents. Further, targeted administration of diagnostic agents via MAC transmembrane channels is also possible. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123; technitium-99 m; iodine-131 and indium-111, nuclides for nuclear magnetic resonance such as fluorine and gadolinium. Other diagnostic agents useful in the invention will be apparent to one of ordinary skill in the art.

As used herein, an effective amount of therapeutic or diagnostic agents administered to cells via MAC transmembrane channels is a dosage large enough to produce the desired therapeutic or diagnostic effect on the cells in which MAC transmembrane channels are formed. An effective amount is not, however, a dosage so large as to cause adverse side effects. Generally, an effective amount of a therapeutic or diagnostic agent may vary with the subject's age, condition, weight and sex, as well as the extent of the condition being treated, and can be determined by one of skill in the art. The dosage may be adjusted by the individual practitioner in the event of any complication.

The active compounds of the present invention may be a pharmaceutical composition having a therapeutically effective amount of a MAC transmembrane channel forming agent optionally included in a pharmaceutically-acceptable carrier. The term "pharmaceutically-acceptable carrier" as used herein means one or more compatible solid or liquid filler, dilutents or encapsulating substances which are suitable for administration to a human or other animal. The term "carrier" denotes an organic or inorganic ingredient, natural or synthetic, with which the active ingredient is combined to facilitate the application. Pharmaceutically acceptable compositions may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group. The components of the pharmaceutical compositions also are capable of being commingled with the molecules of the present invention, and with each other, in a manner such that there is no interaction which would substantially impair the desired pharmaceutical effect.

A variety of administration routes for MAC transmembranes channel forming agents are available. The particular mode selected will depend of course, upon the particular therapeutic or diagnostic agent selected, the severity of the medical disorder being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal, subcutaneous, intravenous, intramuscular, or infusion methodologies.

The compositions containing MAC transmembrane channel forming agents conveniently may be presented in unit dosage form and may be prepared by any of the methods well known in the art of pharmacy. Such methods include the step of bringing the active ingredient into association with a carrier which constitutes one or more accessory ingredients. In general, the compositions are prepared by uniformly and intimately bringing the MAC transmembrane channel forming agents into association with a liquid carrier, a finely divided solid carrier, or both, and then, if necessary, shaping the product.

Injectable compositions and topical preparations are contemplated. Suitable formulations may be found in Remington's Pharmaceutical Sciences (Mack Publishing, Easton, Pa.).

Preferred compositions suitable for parenteral administration conveniently comprise a sterile aqueous preparation of the MAC transmembrane channel forming agents. This aqueous preparation may be formulated according to known methods using those suitable disbursing or wetting agents and suspending agents. The sterile injectable preparation may also be a sterile injectable solution or suspension in a non-toxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono or di-glycerides. In addition, fatty acids such as oleic acid find use in the preparation of injectables.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Dosage may be adjusted appropriately to achieve a desired effect. Generally, daily doses of active compounds can be determined by one of ordinary skill in the art without undue experimentation, in one or several administrations per day, to yield the desired results. In the event that the response in a subject is insufficient at a certain dose, even higher doses (or effective higher doses by a different, more localized delivery route) may be employed to the extent that patient tolerance permits. Multiple doses per day are contemplated to achieve appropriate systemic or targeted levels of compounds. Generally, oral dosages for pharmaceuticals contain 0.01 mg/kg body weight to 1000 mg/kg body weight. It is expected that doses creating systemic blood levels of 20–60 $\mu$g/ml will be appropriate although even smaller doses are contemplated where the agent is targeted as described above.

According to another aspect of the invention, kits for forming MAC transmembrane channels in a cell are provided. The kits contain, in individual containers, a MAC transmembrane channel forming agent comprising an isolated C5b–C6 complement protein complex, isolated C7, C8 and C9 terminal complement proteins, as well as instructions for using the MAC transmembrane channel forming agent in accordance with the methods of the invention. Optionally, the kits include components for preparation of a MAC transmembrane channel forming agent comprising C5b–C6 including isolated CS protein, isolated C6 protein, cobra venom factor, factor B and factor D as well as is C8 and C9 terminal complement proteins and instructions for the prepartion of the C5b–C6 complex.

EXAMPLE 1

Delivery of Dextran to Human Vascular Endothelial Cells

C5b–C6 protein complex was prepared by incubating 60 micrograms of CS (1.0 $\mu g/\mu l$) and 60 micrograms of C6 (1.0 $\mu g/\mu l$) complement proteins with 100 micrograms of cobra venom factor (CVF) (0.5 $\mu g/\mu l$), 30 micrograms of factor B (1.0 $\mu g/\mu l$), 1.5 micrograms of factor D (1.0 $\mu g/\mu l$) and 1 $\mu M$ NiCl$_2$ for 60 minutes at 30° C. C5b–C6 complex was purified by HPLC on a DEAE column. Human vascular endothelial cells (HUVEC) were incubated for 3 minutes at 37° C. in serum-free medium containing 6 units of purified C5b–C6 protein complex and 100 $\mu l$ of a 1.0 $\mu g/\mu l$ stock solution of C7 for a final concentration of 30 $\mu g/\mu l$. A unit is that amount of C5b–C6 required to produce 50% lysis of a 2% hematocrit suspension of human red blood cells. Cells were incubated for five minutes at 37° C., and then 100 $\mu l$ of a 1.0 $\mu g/\mu l$ stock solution of C8 and 100 $\mu l$ of a 1.0 $\mu g/\mu l$ stock solution of C9 (for a final concentration of 30 $\mu g/\mu l$ of each protein) and FITC-dextran (10,000MW) to a final concentration of 10 mg/ml were added to the HUVEC cells for 15 minutes. The cells were washed several times. The whole cell population of HUVEC trapped FITC-dextran after treatment with a sublytic concentration of hMAC. No evidence of cell lysis was detected as measured by the release of lactate dehydrogenase (LDH). There also was no detected evidence of cell toxicity assessed by cell morphology and uptake of trypan blue.

EXAMPLE 2

Incorporation of $^{125}$I-IFNγ Human Red Blood Cell Ghosts (hRBCG)

One milliliter of a cell suspension containing 5×10$^8$ of hRBCG was incubated with $^{125}$I-IFNγ in the presence of one unit of C5b–C6 and C7–C9 in amounts as described above in Example 1 for 30 minutes at 37° C. The uptake of $^{125}$I-IFNγ was 100% higher in hRBCG exposed to C5b–C9 than in hRBCG exposed to C5b–C7 under the same conditions. Incubation of hRBCG with C5b–C7 resulted in the same level of uptake of $^{125}$I-IFNγ as hRBCG that were not exposed to any complement proteins.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A method for treating a subject with a therapeutic or diagnostic agent comprising:

administering to a subject in need of such treatment an effective amount of a non-constitutive membrane attack complex (MAC) transmembrane channel forming agent to form a sublytic amount of MAC transmembrane channels in cells within said subject, and administering substantially simultaneously therewith an effective amount of said therapeutic or diagnostic agent, said therapeutic or diagnostic agent being non-binding to said non-constitutive MAC transmembrane channel forming agent when said non-constitutive MAC transmembrane channel forming agent comprises an antibody.

2. A method as in claim 1 wherein said therapeutic or diagnostic agent is non-binding to said MAC transmembrane channel forming agent.

3. A method as in claim 1 wherein the MAC transmembrane channel forming agent selectively binds to predetermined target cells within the subject.

4. A method as in claim 3 wherein the target cells are cells of the subject.

5. A method as in claim 3 wherein the target cells are cells of an infectious agent within the subject.

6. A method as in claim 1 wherein the MAC transmembrane channel forming agent is isolated C5b–C6 complement protein complex.

7. A method as in claim 1 wherein the therapeutic or diagnostic agent is a therapeutic agent selected from the group consisting of polypeptides, oligonucleotides, toxins, antibiotics, antivirals, antiparasitics, antifungals and antineoplastics.

8. A method as in claim 1 wherein the therapeutic or diagnostic agent is a therapeutic oligonucleotide.

* * * * *